(12) United States Patent
Williams et al.

(10) Patent No.: US 10,358,406 B2
(45) Date of Patent: Jul. 23, 2019

(54) PROCESS AND APPARATUS FOR REMOVING ALDEHYDES FROM ACETONE

(71) Applicants: UOP LLC, Des Plaines, IL (US); AdvanSix Inc., Parsippany, NJ (US)

(72) Inventors: Chad A. Williams, Arlington Heights, IL (US); Michael J. Petragnani, Orefield, PA (US); Russell C. Schulz, Glen Ellyn, IL (US); Daniel R. Wright, Philadelphia, PA (US)

(73) Assignees: UOP LLC, Des Plaines, IL (US); AdvanSix Inc., Pasippany, NJ (US)

( * ) Notice: Subject to any disclaimer, the term of this patent is extended or adjusted under 35 U.S.C. 154(b) by 0 days.

(21) Appl. No.: 16/023,442

(22) Filed: Jun. 29, 2018

(65) Prior Publication Data

US 2019/0002383 A1    Jan. 3, 2019

Related U.S. Application Data

(60) Provisional application No. 62/526,901, filed on Jun. 29, 2017.

(51) Int. Cl.
*C07C 45/80* (2006.01)
*B01D 11/00* (2006.01)
*B01D 11/04* (2006.01)

(52) U.S. Cl.
CPC ........... *C07C 45/80* (2013.01); *B01D 11/043* (2013.01); *B01D 11/0492* (2013.01)

(58) Field of Classification Search
CPC .............................. C07C 45/80; B01D 11/043
See application file for complete search history.

(56) References Cited

U.S. PATENT DOCUMENTS

| | | | |
|---|---|---|---|
| 3,668,256 A | 6/1972 | Brundege | |
| 4,722,769 A | 2/1988 | Chan et al. | |
| 6,303,826 B1 * | 10/2001 | Bhinde | C07C 45/82 568/410 |
| 6,340,777 B1 * | 1/2002 | Aristovich | C07C 45/82 568/411 |

FOREIGN PATENT DOCUMENTS

WO    1997012654 A1    10/1997

OTHER PUBLICATIONS

International Search Report and Written Opinion, PCT/US2018/040052, dated Oct. 25, 2018.

* cited by examiner

*Primary Examiner* — Sikarl A Witherspoon

(57) ABSTRACT

The present invention relates to process and apparatus for removing aldehydes from acetone. More specifically, the present invention relates to a process and apparatus for removing aldehydes from acetone by reacting the aldehydes with caustic in an acetone column and washing the organic phase with a plurality of water streams.

11 Claims, 2 Drawing Sheets

PROCESS AND APPARATUS FOR REMOVING ALDEHYDES FROM ACETONE

PRIORITY CLAIM

This application claims the benefit of U.S. Provisional Application Ser. No. 62/526,901, filed Jun. 29, 2017, entitled Process and Apparatus for Removing Aldehydes from Acetone, which is incorporated herein in its entirety.

FIELD

The present invention relates to process and apparatus for removing aldehydes from acetone. More specifically, the present invention relates to a process and apparatus for removing aldehydes from acetone by reacting the aldehydes with caustic in an acetone column and washing the organic phase with a plurality of water streams.

BACKGROUND

A process for removing aldehydes from acetone is described. Aldehydes are an acetone product impurity from phenol processes which produces both acetone and phenol from cumene. Aldehydes are generated from ethylbenzene, alpha-methylstyrene (AMS), and n-propylbenzene in the cumene feed. Aldehydes are normally removed via reactive distillation by reaction with acetone, catalyzed with caustic. Generating the ideal conditions for this reaction to take place effectively is difficult in practice because aldehyde removal is improved by the presence of more water further up the column, closer to the product tray. However, the acetone product has limitations on the maximum concentration of water. The maximum allowable water, and also aldehyde, are generally decreasing thus making column optimization difficult. A new process to meet product demands is required. In addition, producing a very dry acetone product can allow selling into new markets not previously available, namely electronic-grade acetone. Producing a drier acetone product requires moving the water-rich zone within the finished acetone column (FAC) away from its ideal location, the 'reaction zone,' within the FAC and at the caustic addition point. Whereas new units the column can be made larger to compensate, this is not an economic solution for a majority of the world's existing acetone capacity. This invention solves this problem by allowing a drier acetone product to be made while at the same time achieving high aldehyde removal by the injection of liquid water below the feed tray of the acetone column. This additional water efficiently absorbs aldehydes and aldehyde condensation products (aldols) from the reaction zone and rejects them to the bottom of the acetone column.

SUMMARY

The present invention is a process for removing aldehydes from acetone and provides an acetone product from phenol processes with very low aldehydes. This will improve the quality of phenol units in a technology where differences between designs can be small and difficult to quantify. This can also allow sale of acetone to downstream users not previously possible due to product purity limitations of the current technology.

Water is injected to the lower half of the finished acetone column (FAC). Water acts to possibly condense or more effectively mix, react and remove aldehydes and aldol products within the FAC, allowing aldehydes to be reduced to very low concentrations in the acetone product. Normally, FAC designs have a small flow of water to this general location from condensed steam or sealant liquid from the FAC vacuum system (ejector or LRVP) to recover the acetone in those streams. This invention optimizes the location and flow rate for adding this water to significantly and reliably generate a low-aldehyde acetone product.

DETAILED DESCRIPTION

The following detailed description is merely exemplary in nature and is not intended to limit the application and uses of the embodiment described. Furthermore, there is no intention to be bound by any theory presented in the preceding background or the following detailed description.

Figure 1:
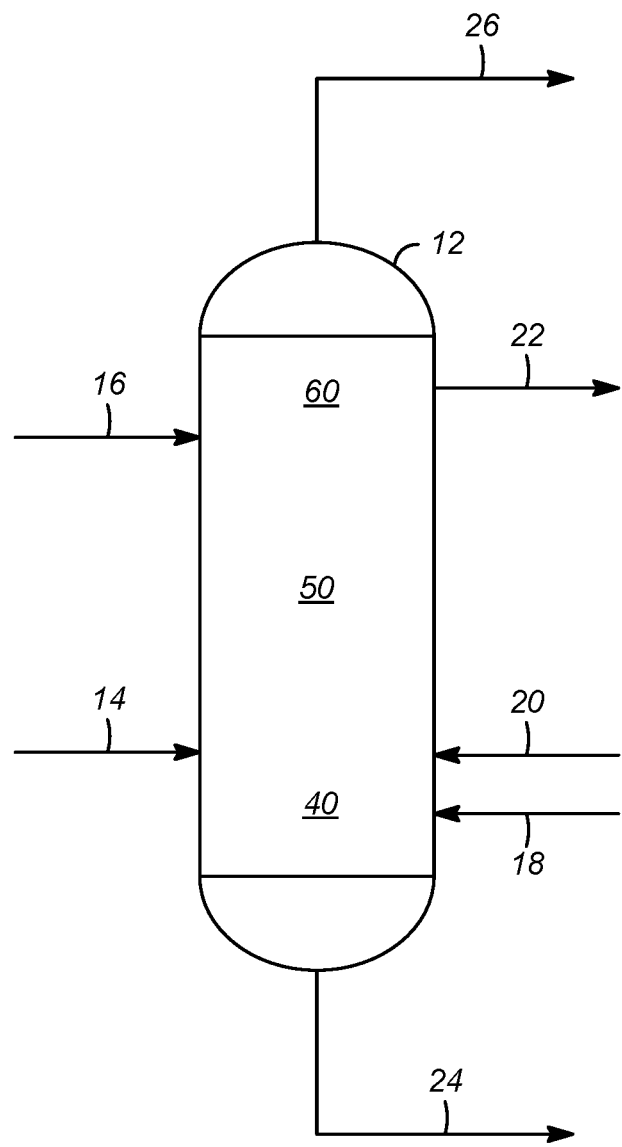
FIG. 1 illustrates a process and apparatus for removing aldehydes from acetone by reacting the aldehydes with caustic in an acetone column and washing the organic phase with a plurality of water streams.

The further description of the process of this invention is presented with reference to the attached FIG. 1. FIG. 1 is a simplified flow diagram of a preferred embodiment of this invention and is not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

The various embodiments described herein relate to process and apparatus for removing aldehydes from acetone by reacting the aldehydes with caustic in an acetone column and washing the organic phase with a plurality of water streams. In accordance with the present invention, the vertical, countercurrent contacting zone is preferably contained in a vessel such as a column 12, which has packing, trays or other convenient means to provide counter-current vapor-liquid contacting. In one example, jetting trays may provide contacting of the organic phase through an aqueous caustic scrubbing solution to remove the organic acid from the organic phase. The contacting zone is preferably operated at a pressure from about atmospheric 50 kPa absolute to about 200 kPa gauge and a temperature from about 10° C. to about 100° C. However, other operating temperatures and pressures may be used in the practice of the present process, but preferably so long as the liquid phase is maintained.

Turning to the FIG. 1, a feed 14 to the acetone column 12. In the example shown in FIG. 1, the feed 14 includes acetone, cumene, water, and aldehydes. However, it is contemplated that the feed may contain other hydrocarbon mixtures. For example, it is contemplated that the feed may contain organic acids, benzene, cumene, phenol, hydroxy-acetone, 2-MBF, acetaldehyde, propionaldehyde, and heavy alkyphenols. The feed 14 enters the column 12 in a vapor state. The feed is below its critical temperature and can be liquefied by compressing it, thus in the vapor state rather than the gas state.

The acetone column 12 comprises a lower portion 40, an intermediate portion 50, and an upper portion 60. The feed 14 enters the acetone column 12 in the intermediate portion 50. The caustic solution 16 enters the acetone column 12 in the upper portion 60 of the acetone column 12. However, it is contemplated that the feed 14 and caustic solution 16 may enter the acetone column 12 at other portions of the column 12.

The aqueous caustic solution which is introduced into the caustic/hydrocarbon contacting zone preferably contains from about 0.5 wt % to about 20 wt % caustic. While various caustic solutions that are known in the art for treating an acetone feed may be used, the preferred caustic solution is an aqueous sodium hydroxide solution. Make-up caustic solutions may have concentrations from about 5 wt % to about 50 wt % caustic. In the example shown in FIG. 1, the sodium hydroxide may comprise 1 wt % of the caustic solution. The flow rate of the aqueous caustic solution used is related to the amount of aldehydes that are being removed from the feed 14.

A first water stream 18 enters the acetone column 12 in the lower portion 40 of the column 12. A second water stream 20 enters the acetone column 12 in the lower portion 40 of the column 12 above the first water stream 18. As the organic feed 14 moves up the acetone column 12 the aldehyde in the organic feed 14 becomes entrained with the caustic 16 and then is contacted with the first water stream 18 and the second water stream 20. Within the column 12, the aldehydes undergo a condensation reaction with acetone to form an aldol in the aqueous phase where the reaction occurs. The caustic catalyzes the reaction of the aldehyde with the acetone to make an aldol. Some of the aldol transfers to the cumene-rich organic phase and is rejected to the bottom of the FAC. The remaining aldol continues to react with the acetone, catalyzed by caustic, to form a heavy which transitions to the organic phase and is rejected to the bottom of the FAC. The presence of sufficient aqueous phase is critical to allow the interaction of aldehydes and acetone with the caustic catalyst. Therefore, management of the aqueous phase within the finished acetone column is also critical. Additional water below the feed trays helps better manage the aqueous phase within the column while still generating an acetone product low in water. Once the organic feed reaches the top of the column 12, a clean, mainly aldehyde free organic phase exits the top of the column 12 in the product stream 22. An overhead vapor stream 26 also exits the top of the column 12.

A portion of the product stream 22 may be recycled back to the feed 14. However, in some embodiments it may be an overhead liquid that is recycled, not the acetone product. The recycled product may be mixed with the feed 14 before entering the acetone column 12, or the recycled product feed and the feed 14 may enter the acetone column 12 at distinct inlets. A second product stream 24 exits from the bottom of the column 12. The second product stream 24 comprises water, cumene, caustic, and aldehydes.

The column 12 is a finished acetone column having a plurality of trays. As described earlier, in one example, jetting trays may provide contacting of the organic phase through an aqueous caustic scrubbing solution to remove the aldehyde from the organic phase. In one embodiment, the column 12 has 60 trays. In this example, the first and second water streams are injected into the column below the line for injecting the feed stream. More specifically, the feed stream may be injected into the column in the 51st tray, the first water stream and the second water streams may be injected into the column in the 53rd tray. In all embodiments, it is contemplated that the water streams must be injected into the column below the feed. This location provides the optimal placement for the aldehydes to react with acetone, catalyzed by the caustic solution. Then the water also scrubs additional aldehydes out of the feed, thus removing the aldehydes from the acetone.

While the invention has been described with what are presently considered the preferred embodiments, it is to be understood that the invention is not limited to the disclosed embodiments, but it is intended to cover various modifications and equivalent arrangements included within the scope of the appended claims.

Figure 2:
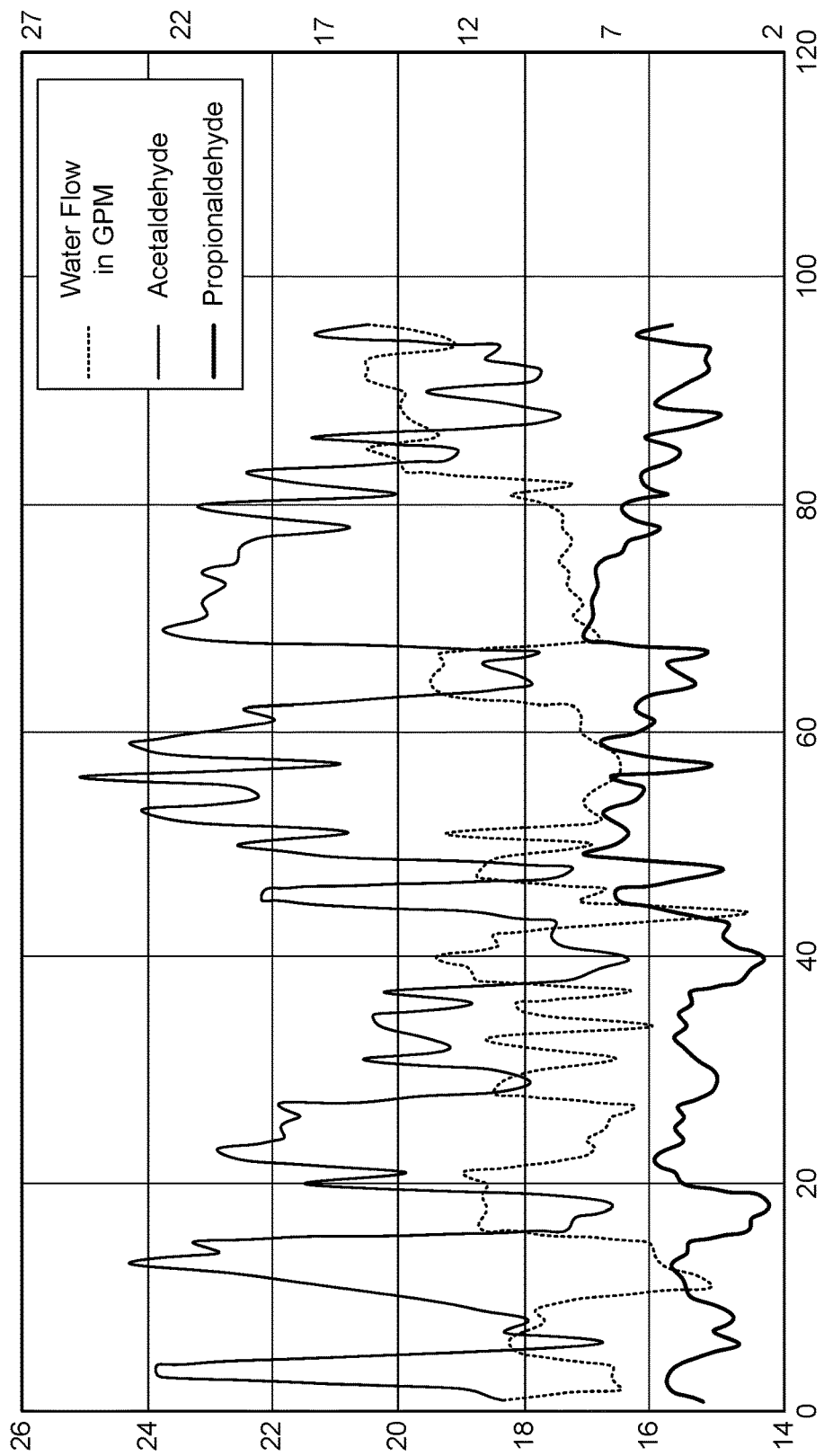
FIG. 2 illustrates the correlation between the amount of water and the amount of aldehydes.

FIG. 2 demonstrates the benefits of the process claimed in this invention. As the graph in FIG. 2 illustrates, as the water flow increases, both the acetaldehyde and the propionaldehydes decrease.

Specific Embodiments

While the following is described in conjunction with specific embodiments, it will be understood that this description is intended to illustrate and not limit the scope of the preceding description and the appended claims.

A first embodiment of the invention is a process for removing aldehydes from acetone, comprising introducing a feed stream containing at least one organic compound in a column; introducing an aqueous caustic scrubbing solution into the column; introducing a first water stream into a water wash section of the column; introducing a second water stream into the water wash section of the column; removing spent aqueous caustic and aldehyde solution from the column; and removing an organic product from the water wash section of the column having a reduced level of aldehydes relative to the feed stream. An embodiment of the invention is one, any or all of prior embodiments in this paragraph up through the first embodiment in this paragraph, wherein the feed stream comprises acetone, cumene, water, and aldehydes. An embodiment of the invention is one, any or all of prior embodiments in this paragraph up through the first embodiment in this paragraph, wherein the organic compound is acetone. An embodiment of the invention is one, any or all of prior embodiments in this paragraph up through the first embodiment in this paragraph, wherein the process removes about 99% of aldehydes. An embodiment of the invention is one, any or all of prior embodiments in this paragraph up through the first embodiment in this paragraph, wherein the caustic scrubbing solution contains about 0.5 wt % caustic to about 20 wt % caustic. An embodiment of the invention is one, any or all of prior embodiments in this paragraph up through the first embodiment in this paragraph, wherein the caustic scrubbing solution contains about 1% of caustic. An embodiment of the invention is one, any or all of prior embodiments in this paragraph up through the first embodiment in this paragraph, wherein the column is a finished acetone column. An embodiment of the invention is one, any or all of prior embodiments in this paragraph up through the first embodiment in this paragraph, wherein the column is operated at a pressure from about −0.50 kg/cm2 (g) to about 2.0 kg/cm2(g) and a temperature from about 40° C. to about 100° C. An embodiment of the invention is one, any or all of prior embodiments in this paragraph up through the first embodiment in this paragraph, wherein the first water stream comprises water and about 10% acetone. An embodiment of the invention is one, any or all of prior embodiments in this paragraph up through the first embodiment in this paragraph, wherein the second water stream is 100% water and is introduced to the column at a rate of 0.1 kg water/kg acetone product to about 0.4 kg water/kg acetone product. An embodiment of the invention is one, any or all of prior embodiments in this paragraph up through the first embodiment in this paragraph, wherein the aldehydes react with acetone, catalyzed by the caustic scrubbing solution inside the column to form an aldol or heavy, soluble in the cumene-rich organic phase, which is rejected to the bottom of the column.

A second embodiment of the invention is an apparatus for removing aldehydes from acetone, comprising; a line for introducing a feed stream containing at least one organic compound into a column; a line for introducing a caustic scrubbing solution in the column; a line for introducing a first water stream into a water wash section of the column; a line for introducing a second water stream into the water wash section of the column; a line for removing spent caustic and organic solution from the column; a line for removing an organic product form the water wash section of the column wherein the organic product has a reduced level of aldehydes relative to the feed stream. An embodiment of the invention is one, any or all of prior embodiments in this paragraph up through the second embodiment in this paragraph, wherein the organic feed comprises acetone, cumene, water, and aldehydes. An embodiment of the invention is one, any or all of prior embodiments in this paragraph up through the second embodiment in this paragraph, wherein the organic compound is acetone. An embodiment of the invention is one, any or all of prior embodiments in this paragraph up through the second embodiment in this paragraph, wherein the column is operated at a pressure from about −0.36 kg/cm2(g) to about 3.0 kg/cm2(g) and a temperature from about 40° C. to about 100° C. An embodiment of the invention is one, any or all of prior embodiments in this paragraph up through the second embodiment in this paragraph, wherein the column comprises a plurality of trays. An embodiment of the invention is one, any or all of prior embodiments in this paragraph up through the second embodiment in this paragraph, wherein the column comprises 60 trays. An embodiment of the invention is one, any or all of prior embodiments in this paragraph up through the second embodiment in this paragraph, wherein the line for introducing a first water stream is injected into the column below the line for injecting the feed stream. An embodiment of the invention is one, any or all of prior embodiments in this paragraph up through the second embodiment in this paragraph, wherein the line for introducing a second water stream is injected into the column below the line for injecting the feed stream. An embodiment of the invention is one, any or all of prior embodiments in this paragraph up through the second embodiment in this paragraph, wherein the feed stream is injected into the column in the $51^{st}$ tray, the first water stream and the second water stream is injected into the column in the $53^{rd}$ tray.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for removing aldehydes from acetone, comprising:
    introducing a feed stream containing at least one organic compound in a column;
    introducing an aqueous caustic scrubbing solution into the column;
    introducing a first water stream into a lower portion of the column;
    introducing a second water stream into the lower portion of the column;
    removing spent aqueous caustic and aldehyde solution from the column; and
    removing an organic product from an upper portion of the column having a reduced level of aldehydes relative to the feed stream.

2. The process of claim 1, wherein the feed stream comprises acetone, cumene, water, and aldehydes.

3. The process of claim 1, wherein the organic compound is acetone.

4. The process of claim 1, wherein the process removes about 99% of aldehydes.

5. The process of claim 1, wherein the caustic scrubbing solution contains about 0.5 wt % caustic to about 20 wt % caustic.

6. The process of claim 1, wherein the caustic scrubbing solution contains about 1% of caustic.

7. The process of claim 1, wherein the column is a finished acetone column.

8. The process of claim 1, wherein the column is operated at a pressure from about −0.50 kg/cm2(g) to about 2.0 kg/cm2(g) and a temperature from about 40° C. to about 100° C.

9. The process of claim 1, wherein the first water stream comprises water and about 10% acetone.

10. The process of claim 1, wherein the second water stream is 100% water and is introduced to the column at a rate of 0.1 kg water/kg acetone product to about 0.4 kg water/kg acetone product.

11. The process of claim 1, wherein the aldehydes react with acetone, catalyzed by the caustic scrubbing solution inside the column to form an aldol or heavy, soluble in the cumene-rich organic phase, which is rejected to the bottom of the column.

* * * * *